United States Patent [19]
Vass et al.

[11] Patent Number: 5,985,268
[45] Date of Patent: Nov. 16, 1999

[54] GAMMA-IRRADIATED BACTERIAL PREPARATION HAVING ANTI-TUMOR ACTIVITY

[75] Inventors: Arpad A. Vass, Oak Ridge; Richard L. Tyndall, Clinton, both of Tenn.; Peggy Terzaghi-Howe, Montrose, Colo.

[73] Assignee: Lockheed Martin Energy Research Corp., Oak Ridge, Tenn.

[21] Appl. No.: 08/929,648

[22] Filed: Sep. 15, 1997

[51] Int. Cl.⁶ .............................. A01N 63/00; C12Q 1/02; C12N 13/00; C12N 1/20
[52] U.S. Cl. ..................... 424/93.47; 435/29; 435/173.8; 435/253.3; 435/874
[58] Field of Search .................... 435/29, 253.3, 435/173.8, 874; 424/93.47

[56] References Cited

U.S. PATENT DOCUMENTS

| | | | |
|---|---|---|---|
| 4,440,752 | 4/1984 | Munakata et al. | 424/118 |
| 4,940,582 | 7/1990 | Iwasaka et al. | 424/115 |
| 5,420,035 | 5/1995 | Tyndall | 435/252.1 |
| 5,518,919 | 5/1996 | Tyndall | 435/262.5 |
| 5,545,542 | 8/1996 | Nakajima et al. | 435/128 |
| 5,702,702 | 12/1997 | Santoli et al. | 424/93.71 |

FOREIGN PATENT DOCUMENTS 60-169499  9/1985  Japan .
739096  6/1980  U.S.S.R. .

OTHER PUBLICATIONS

Roberts et al. "Inhibition of mouse retroviral disease by bioactive glutaminase–asparaginase", J. Gen. Virol, 1991, 72(2), pp. 299–305.

Roberts J. "Purification and properties of a highly potent antitumor glutaminase–asparaginase from Pseudomonas 7A", The Journal of Biological Chemistry 1976, vol. 251, No. 7. pp. 2119–2123.

*Primary Examiner*—Sandra E. Saucier
*Assistant Examiner*—Vera Afremova
*Attorney, Agent, or Firm*—Quarles & Brady LLP

[57] ABSTRACT

A bacterial preparation from Pseudomonas species isolated #15 ATCC 55638 that has been exposed to gamma radiation exhibits cytotoxicity that is specific for neoplastic carcinoma cells. A method for obtaining a bacterial preparation having antitumor activity consists of suspending a bacterial isolate in media and exposing the suspension to gamma radiation. A bacterial preparation of an aged culture of an amoeba-associated bacteria exhibits anti-reverse transcriptase activity. A method for obtaining a bacterial preparation having anti-reverse transcriptase activity from an amoeba-associated bacterial isolate grown to stationary phase is disclosed.

7 Claims, No Drawings

GAMMA-IRRADIATED BACTERIAL PREPARATION HAVING ANTI-TUMOR ACTIVITY

STATEMENT REGARDING FEDERALLY SPONSORED RESEARCH OR DEVELOPMENT

This invention was made with government support under contract DE-AC05-960R22464, awarded by the United States Department of Energy to Lockheed Martin Energy Research Corporation, and the United States Government has certain rights in this invention.

CROSS REFERENCE TO RELATED APPLICATIONS

Not applicable.

BACKGROUND OF THE INVENTION

Within the pharmaceutical industry and medical community, there is an ongoing interest in the development of new chemotherapeutics for the treatment of persons with various types of cancer. Great strides have been made in the treatment of certain types of cancer, whereas certain other cancers remain refractory to treatments that are currently available.

In general, most cancer treatments operate by destroying the cancerous cells or by inhibiting cellular proliferation. Unfortunately, most chemotherapeutic agents known to the art lack specific toxicity, in that they are toxic for dividing normal cells, as well as malignant cells. Consequently, persons undergoing a regimen of chemotherapy may suffer severe side effects or even death as a consequence of nonspecific cytotoxicity. Recently, biological preparations from natural sources (e.g., Taxol, which is derived from the yew tree) have shown promise as a new source of more specific chemotherapeutic agents.

We are currently experiencing a worldwide epidemic of acquired immune defiency syndrome (AIDS), a disease caused by the retrovirus human immunodeficiency virus (HIV). As of December, 1994, more than one million cases of AIDS had been reported to the World Health Organization (WHO). The WHO has estimated that actual AIDS cases as of 1994 totalled more than 4.5 million worldwide. An estimate by the WHO predicts that there will be 10 million AIDS cases and 30–40 million people infected with HIV worldwide by the year 2000.

The human immunodeficiency virus, a lentivirus, is a member of the Retroviridae family of retroviruses. This family includes other members that are causal agents of devastating disease of humans. For example, certain cancers are caused by oncornaviruses, oncogenic viruses that cause transformation of cells. Retroviruses are particularly refractory to treatment, largely because of their unique replication strategy.

Retroviruses are single-stranded RNA viruses. The virions of retroviruses include reverse transcriptase, an enzyme that catalyzes the synthesis of a single-stranded DNA molecule, using the single-stranded viral RNA as a template. Second strand synthesis, also catalyzed by reverse transcriptase, yields a double-stranded DNA provirus that integrates into the host's genome. In the case of lentiviruses such as HIV, the virus may lie dormant for a period of several years before becoming activated again.

The human immuondeficiency virus infects CD4+ T lymphocytes, cells that play an important role in combatting infections. Proliferation of HIV within the T cells results in destruction of the cells and interruption of the cells' normal function. As a consequence, people with AIDS are susceptible to opportunistic infections and the development of neoplasms.

Millions of dollars have been directed toward the development of drugs for the treatment of persons infected with the human immunodeficiency virus (HIV). One promising class of chemotherapeutics includes inhibitors of reverse transcriptase, an enzyme that is required for the replication of HIV and other members of the Retroviridae family of viruses.

What is needed in the art are chemotherapeutic agents that are specific for cancerous cells. Also needed in the art are novel drugs that can effectively inhibit reverse transcriptase.

BRIEF SUMMARY OF THE INVENTION

It is an object of the present invention to provide a chemotherapeutic agent that is effective against carcinoma cells and that does not exhibit cytotoxicity against normal cells.

It is a further object of the present invention to provide a chemotherapeutic agent that can effectively inhibit reverse transcriptase and prevent infection of cells with the human immunodeficiency virus.

The present invention is drawn to a bacterial preparation, derived from a bacterial isolate having the characteristics of bacterial isolate #15 (ATCC No. 55638), an amoeba-associated bacterial species, wherein the preparation exhibits cytotoxicity specific for neoplastic carcinoma cells.

The present invention is also a method for obtaining a bacterial preparation having anti-tumor activity from a bacterial culture, comprising growing a culture of a bacterial isolate having the characteristics of bacterial isolate #15 (ATCC No. 55638) in the presence or absence of an amoeba species and exposing the culture to an effective dose of gamma radiation.

The present invention is also a bacterial preparation made from a bacterial isolate having the characteristics of bacterial isolate #15 (ATCC No. 55638), an amoeba-associated bacterial species, wherein the preparation exhibits the ability to inhibit reverse transcriptase.

The present invention is also a method for obtaining an anti-reverse transcriptase preparation from a bacterial culture, comprising growing a culture of a bacterial isolate having the characteristics of Pseudomonas species isolate #15 (ATCC No. 55638) to stationary phase.

BRIEF DESCRIPTION OF THE SEVERAL VIEWS OF THE DRAWINGS

Not applicable.

DETAILED DESCRIPTION OF THE INVENTION

One aspect of the present invention is a bacterial preparation having antitumor activity (AT), wherein the preparation is made from a culture of a bacterial isolate having the characteristics of isolate #15 (ATCC No. 55638), an amoeba-associated bacteria, wherein the preparation exhibits cytotoxicity specific for neoplastic carcinoma cells.

Bacterial isolate #15 (ATCC 55638) was found to be effective in the practice of the present invention. The isolation and characterization of isolate #15 is disclosed in U.S. Pat. No. 5,518,919, which is incorporated by reference herein. Bacterial isolate #15 (ATCC 55638) has not been definitively classified, but it is a Pseudomonas-like species. The isolate will be referred to herein as Pseudomonas species isolate #15 (ATCC 55638). This designation is not intended to be limiting should the organism be later classified as belonging to a genus other than Pseudomonas.

It is anticipated that other isolates having the characteristics of Pseudomonas species isolate #15 (ATCC 55638) will be useful in this invention. Pseudomonas species isolate #15 (ATCC 55638) is characterized as an amoeba-associated bacterial species that produces a product or products having anti-carcinoma activity when exposed to an effective dose of gamma radiation.

An "amoeba-associated bacterial species" is defined herein as a bacterial species that is found to coexist with a free-living amoeba in an ecto- or endosymbiotic relationship.

Partial characterization of AT has revealed that AT has the following properties: 1) AT is not directly cytotoxic, in that initial inhibitory effects are not observed until several days after exposure and the inhibitory effect appears to be one of blocking cell proliferation; 2) the inhibitory effect of this agent appears to be irreversible in that removal of the agent after several days does not result in the regrowth of the affected cells; 3) the toxicity of this agent is cell-type specific, and in particular, appears to primarily affect carcinoma-derived cell populations which are the most clinically relevant cancers in humans; 4) this agent is minimally toxic to proliferating normal cell populations in culture and virtually non-toxic to normal cells in vivo and high density normal primary cells in culture; 5) this product has no inherent mutagenic or toxic characteristics on normal cells as seen using SCE and Ames assays; and 6) this product is activated by exposure to high doses of radiation by some yet unidentified mechanism.

An "effective dose of gamma radiation" is that dose of gamma radiation required to afford a significant increase in anti-tumor activity, relative to untreated cells. The examples below demonstrate that a gamma radiation dosage of approximately 1.5 mR, delivered at a rate of 0.3 mR over a 5 hour time period, is effective in activating AT in a cell suspension of bacterial isolate #15. It is likely that a 1.5 mR dose delivered at a higher rate over a shorter time period, or at a lower rate over a longer time period, would be effective in activating AT. It is expected that dosages that are higher or lower than 1.5 mR also will be effective in activating AT.

"Anti-tumor activity", as used herein, refers to the ability to significantly inhibit the proliferation of sensitive neoplastic carcinoma cells. As described in the examples below, the inhibitory effect of AT was quantitated using LT-1 carcinoma cells. Depending upon the AT preparation, the percentage of LT-1 cells surviving treatment with AT was at most about 92% (Table 4). Preferably, the percentage of LT-1 cells surviving treatment with AT was at most about 60%. Most preferably, as few as about 10%, or even as few as about 2 to 4% of AT-treated LT-1 cells survive exposure to the anti-tumor activity.

The examples demonstrate that the bacterial preparation of the present invention specifically inhibits proliferation of a number of different neoplastic carcinoma cells in vitro. The tested AT preparations were at least about 8 times more effective in inhibiting cellular proliferation of human- and rat-derived carcinomas than in inhibiting proliferation of normal cells. Preferably, the AT preparation is at least about 16 times more effective in inhibiting cellular proliferation of human- and rat-derived carcinomas than normal cells. Most preferably, the AT preparation is about 40 times more effective in inhibiting cellular proliferation of human- and rat-derived carcinomas than normal cells.

Two methods for culturing the bacteria to obtain the anti-tumor preparation are described in detail in the examples. Briefly, the center of a plated culture of bacterial isolate ATCC 55638 is seeded with *Acanthamoebae royreba* (RR); following aerobic incubation for 3–4 days, the bacteria are harvested, suspended in a suitable liquid medium and exposed to gamma radiation. Alternatively, the antitumor activity may be obtained by growing the bacteria in a liquid culture for two days, followed by gamma radiation exposure. The culture conditions under which the bacterial isolate is grown are not known to affect AT production. The present invention is intended to encompass AT produced by bacteria grown under suitable culture conditions that vary from those disclosed herein.

To obtain the AT activity, the bacterial culture was treated as described in detail in the examples. Efforts to purify and characterize the anti-tumor activity biochemically are currently underway. Preliminary results are described in the examples. The chemical nature of the compound or compounds responsible for the anti-tumor activity has not been determined. However, it is expected that the purification and characterization of the activity will be possible using standard methods known to one skilled in the art. Therefore, the present invention is intended to encompass a purified anti-tumor activity obtained from a gamma-irradiated culture of a of bacterial isolate #15.

Another aspect of the present invention is an anti-reverse transcriptase preparation comprising an aged culture of a bacterial isolate, the isolate having the characteristics of Pseudomonas species isolate #15 (ATCC No. 55638), an amoeba-associated bacteria, wherein the preparation inhibits the RNA-dependent DNA polymerase activity of reverse transcriptase.

Pseudomonas species isolate #15 (ATCC 55638) was found to be effective in the practice of the present invention. It is anticipated that cultures of other isolates having the characteristics of Pseudomonas species isolate #15 will be useful in this invention. Pseudomonas species isolate #15 is characterized by its association with amoeba species and by the ability to produce a substance or substances having anti-reverse transcriptase activity when grown to stationary phase.

By "aged culture" it is meant that the culture is allowed to grow until stationary phase is reached. In the examples below, the bacterial cultures were allowed to grow for about 4 days in TSB at room temperature. The number of days that it takes a bacterial culture to reach a particular phase of growth is dependent on a number of factors, including the medium in which the bacteria are cultured, the temperature, and aeration. Varying these parameters may affect the time it takes for the culture to reach stationary phase. Aged cultures obtained using such variations in culture conditions are within the scope and spirit of the present invention.

A method for obtaining the anti-reverse transcriptase preparation is described in detail in the examples. Briefly, a bacterial isolate having the characteristics of Pseudomonas species isolate #15 is grown in a suitable liquid medium to stationary phase. The bacterial culture was treated as described in detail below. Efforts to purify and characterize the anti-reverse transcriptase activity are currently underway. It is expected that the purification and characterization of the activity can be accomplished using standard methods known to one skilled in the art. The present invention is intended to encompass a purified anti-reverse transcriptase activity obtained from an aged culture of a bacterial isolate having the characteristics of Pseudomonas species isolate #15.

METHODS

Production of Anti-Tumor Activity.

A bacterial preparation containing anti-tumor activity (AT) was obtained as follows. Tryptic soy agar (TSA) plates were spread with the bacterial culture Pseudomonas species isolate #15 (ATCC No. 55638). The plates were incubated at room temperature for two days. Following the initial two day incubation, several drops of a suspension of Acanthamoebae royreba (RR) ($1\times10^5$/drop) in 712 medium (ATCC Media Handbook. First edition, 1984. Cote, R., ed. American Type Culture Collection, Rockville, Md.) were applied to the center of the plates. The plates were incubated aerobically at 35° C. for two days. The bacterial cells were harvested, taking care to avoid harvesting amoebae growth, transferred to screw cap glass test tubes containing 5 ml 712 medium, and resuspended. The suspension was exposed to 1.5 mR gamma irradiation (3.0 mR $h^{-1}$ for 5 hours.) Alternatively, an antitumor preparation can by obtained by growing a broth culture of isolate #15 alone in tryptic soy broth (TSB) at room temperature with minimal additional aeration supplied by a slow speed (40 rpm) rotatory shaker for two days and exposing the cultured cells to 1.5 mR gamma irradiation (3.0 mR $h^{-1}$ for 5 hours).

Evaluation of Toxicity of AT Activity

The toxicity of AT was examined using a variety of cultured normal and neoplastic cell populations of mouse, rat, and human origin (Table 1). Cells were seeded at clonogenic densities in 6-well plates (Costar, Cambridge, Mass.). The plates were incubated for 24 h at 37° C. in a humidified chamber with 5% $CO_2$. Aliquots of AT ranging from 0 to 80 μl were added to duplicate wells, and the cells were incubated for one week at 37° C. The cells were fixed, stained with Giemsa, and the number of surviving cell colonies were scored. The fraction of cells surviving treatment with AT was determined by dividing the number of cells present in wells that received AT by the number of cells present in untreated control wells. The lethal concentration ($LC_{50}$) was calculated by plotting surviving cell fraction as a function of AT concentration (v/v, in/μl $l^{-1}$). The $LC_{50}$ is the concentration at which 50% of the cell colonies were killed.

TABLE 1

Cell Populations Tested for Sensitivity to AT Toxicity

| Designation | Species | Description |
| --- | --- | --- |
| Mouse Cells | | |
| LT-1 | Mouse | Mammary Carcinoma |
| Normal Rat Cells | | |
| NTEC | Rat | Normal Tracheal Epithelial Cells (Primary Cultures) |
| RFb | Rat | Normal Tracheal Fibroblasts |
| Neoplastic/Preneoplastic Rat Cells | | |
| BaP-A | Rat | Squamous Cell Carcinoma |
| IC-12 | Rat | Undifferentiated Tracheal Carcinoma |
| IC-1 | Rat | Preneoplastic Tracheal Cell Line |
| XR600 | Rat | Preneoplastic Tracheal Cell Line |

TABLE 1-continued

Cell Populations Tested for Sensitivity to AT Toxicity

| Designation | Species | Description |
| --- | --- | --- |
| Human Tumors | | |
| SA052 | Human | Osteosarcoma |
| A549 | Human | Lung Carcinoma |
| Hu292 | Human | Lung Carcinoma |

In order to evaluate the effect of cell density or cell proliferation on the toxic response of cells to AT, some cell populations were "center plated" such that all cells were concentrated within a small area in the center of seeded wells. Under these conditions, cell proliferation is minimized, and cell-cell contact is optimized.

Evaluation of Plating Efficiency and Dose-response Curve.

The plating efficiency of mouse mammary carcinoma (LT-1) cells and a dose-response curve for AT were determined. The plating efficiency was determined by trypsinization of a culture of LT-1 cells and enumeration using a hemocytometer chamber counting method. In 6-well tissue culture plates (Costar, Cambridge, Mass.), cells were plated in triplicate at densities of 100 and 200 cells/well in 1.5 ml Ham's Medium (Gibco, BRL, Grand Island, N.Y.) supplemented with fetal calf serum, penicillin, streptomycin, and glutamine (Complete medium). The cells were incubated 4 to 5 days at 37° C. in 5% $CO_2$. After incubation, the medium was removed and the cells were gently washed using physiologic saline. The cells were then fixed in methanol for 10 min at room temperature and stained with Giemsa stain (methanol:Giemsa stain:water, 1:1:23, v/v/v) for 10 min at room temperature, washed 3 times with distilled water, air dried, and counted. A plating efficiency of from about 71–80% was observed.

To determine the dose-response curve, 100 and 300 cells/well in 1.5 ml Ham's Complete medium were plated in 6-well plates. The plates were incubated at 35° C. in 5% $CO_2$. After 24 h, from 0.25 to 5 μl of AT from Batch 5 (irradiated isolate #15 cells grown in the presence of amoeba) was added to the cells. The cells were incubated for 5 days and Giemsa-stained, as described above.

Characterization of AT Using Enzymatic Digestions.

For preliminary characterization of AT, broad range enzymatic digestions were performed (Table 2) using protease, lipase, α-amylase, and lipoprotein lipase (Sigma Chemical Company, St. Louis, Mo.). Stock Solutions (25%) of protease and lipase were made in 0.1 M Tris-HC1 (pH 8). Following enzymatic treatment of AT, enzyme activity was neutralized with one of several alternative treatments (Table 2). Untreated AT in TSB was used as a control to identify loss of AT activity resulting from the neutralization treatment. Following exposure to digestion enzymes and neutralization, samples were tested for AT activity using LT-1 cells, as described previously.

TABLE 2

| Enzyme | Concentration | Time | Temp | Enzyme Inhibited with |
| --- | --- | --- | --- | --- |
| Protease | 1%, 5% | 10 min. | 37° C. | 10% TCA |
| Lipase | 1%, 5% | 30 min. | 25° C. | boiling 1 min. |
| Amylase | 1%, 5% | 10 min. | 90° C. | 10% TCA |
| Lipoprotein lipase | 1%, 5% | 30 min. | 25° C. | boiling 1 min. |

Because it appeared that the neutralization treatments alone were interfering with AT activity, a milder neutralization treatment was sought. Those treatments, summarized in Table 3, were performed to determine the minimum treatment that would inactivate enzyme activity. Oxidase and catalase were utilized as test enzymes in these experiments. The least destructive neutralization treatment, 1% TCA, was able to neutralize enzyme activity and was chosen for further experiments requiring enzyme neutralizations. The enzymatic digestion experiment was repeated with the following modification: Using Batch 4 (isolate #15 grown in the presence of RR), Batch 5 (isolate 15 alone), and Batch 5 (15+RR), 0.5 ml of each was boiled 1 min or autoclaved 10 min as controls. Each was treated with 1% of the 4 enzyme treatments (Table 2) and neutralized with 1% TCA.

TABLE 3

| Treatment of AT | Catalase | Oxidase |
| --- | --- | --- |
| No treatment | + | + |
| 100° C., 1 min. | − | − |
| 100°, 5 min. | − | − |
| 1% TCA | − | − |
| 3% TCA | − | − |
| 5% TCA | − | − |
| 7.5% TCA | − | − |

Characterization of AT Using Extraction Procedures.

Isolation of AT was attempted using several extraction methods.

Lipid extraction. A culture of bacterial isolate 15 in TSB broth and sterile TSB broth were extracted overnight with 2:1 MeOH/CHCl$_3$. The organic phase was removed and fractionated on silicic acid columns into neutral, glycolipid, and phospholipid fractions. Fractions were dried under a stream of N$_2$.

Protein, carbohydrate, lipid extraction. Batch 4 (bacterial isolate 15 grown in the presence of amoeba) was used for extraction of AT; a 2 ml aliquot served as an untreated control. A three ml aliquot of AT was transferred to each of 2 tubes and the tubes were placed in an ice bath; 10 ml of ice-cold 20% TCA was added to each tube and mixed by inversion; the tubes were placed on ice for 5 min. to allow precipitation to occur. The tubes were centrifuged for 15 min. at 8700×g, and the supernatant was transferred to a 25-ml tube. Four ml of ice-cold 10% TCA was added to the tubes containing the precipitate and the tubes were centrifuged again. The supernatant from the second treatment was combined with that previously obtained. The supernatant contained carbohydrates and "small molecules."

The precipitate was resuspended in 10 ml ice-cold 10% TCA and vortexed. A 5-ml aliqout was reserved for lipid extraction and a 5-ml aliqout was used for protein extraction. For the protein extraction, 5 ml water was added to the tube to obtain 5% TCA. The tube was heated at 80° C. for 30 min. and cooled on ice for 30 min. The contents of the tube were filtered through a Millipore HV 0.45 $\mu$m filter, the test tube was washed twice with 2 ml ice-cold 10% TCA, and the wash was filtered. The filter was then washed with 3 ml ice-cold 70% ethanol, twice with 5 ml 70% ethanol at 45° C., twice with 5 ml ethanol:diethyl ether (1:1) at 45° C., and once with 5 ml diethyl ether.

For extraction of lipids, the 5 ml fraction obtained as described above was filtered through a 0.45 $\mu$m Millipore HV filter. The filter was washed twice with 2 ml ice-cold 10% TCA, washed with 3 ml ice-cold 70% ethanol, and the filtrate discarded. The entire filter assembly was warmed to 45° C. Ten ml 70% ethanol at 45° C. was added and allowed 10 min. to pass through filter. The filtrate was saved. The filter was washed with two to five volumes of ethanol:diethyl ether (1:1, v:v) at 45° C. allowing 10 min. for the solvents to pass through the filter. The wash filtrates were combined with the above filtrates.

Detection of Apoptotic Cells and Peroxidase Activity.

Apoptosis is a regulatory response of inducible cells to an inducing stimulus, and can be measured by peroxidase staining and peroxidase activity. In peroxidase staining, peroxidase (catalase) is exposed to and reacts with a chromogenic substrate allowing the apoptotic cells to be stained. Two sets of Flaskette chamber slides (NUNC, Naperville, Ill.) were filled with 1.5 ml of Ham's Complete Medium and inoculated with 0.5×10$^6$ cells. The chambers were incubated at 35° C. in a 5% CO$_2$ atmosphere for several days until a satisfactory monolayer of cells was formed. These cells were treated with 50 $\mu$l of unpurified AT and reincubated for 4 days. The medium was removed from the slide chambers, and the cells washed with phosphate-buffered saline (PBS). Following fixation in 10% neutral buffered formalin for 10 min. at RT, the slides were washed 3 times with distilled water for 5 min. per wash. One set of slides was stained with 0.05% diaminobenzidine (DAB) to which 0.02% H$_2$O$_2$ was added immediately before it was applied to the specimen. The slides were stained for 3–6 min, washed 3 times with distilled water and counterstained with methyl green for 10 min at RT. The counterstain was removed by washing the slides 3 times in distilled water then 3 times with 100% butanol. The specimen was dehydrated in 3 changes of xylene for 2 min. each and mounted under a glass coverslip.

For peroxidase activity, the second set of slides was washed, fixed, rinsed in PBS, immersed in 2% H$_2$ $_{O2}$, and examined for liberation of oxygen by the appearance of bubbles.

ALZET Pumps for In Vivo Delivery of AT.

Experiments with ALZET pumps were conducted to evaluate the timed release of AT for in vivo studies. Two ALZET pumps were soaked in Ham's Complete medium for 24 h. The pumps were removed, drained, and filled with 150–200 $\mu$l AT, washed 2–3 times with medium, and placed in 5 ml of medium. After 6 h. and 24 h., the medium was harvested from the respective pumps. Dilutions of this medium were made and used to replace the medium in a 24 h. culture of LT-1 cells plated at 200 cells/well. The plates were reincubated at 37° C. in 5% CO$_2$. After 5 days, the plates were removed and the cells were stained as previously described. A control plate, consisting of 200 cells/well treated with from 0.25–2.0 $\mu$l of AT, was included.

Silastic Pellets for In Vivo Delivery of AT.

Silastic pellets impregnated with AT were investigated for timed release of AT in vivo. Silastic pellets were polymerized in the presence of 10 $\mu$l lyophilized AT per pellet. This pellet was then soaked in 6 ml Ham's Complete Medium at 37° C. in 5% CO$_2$. After 6 h, 3 ml of medium was removed and incubation of the pellet was continued for 18 h in the remaining 3 ml. AT activity was then assayed in both the 6 h and 24 h samples using LT-1 cells, as described above.

Salmonella Mutagenicity Testing.

AT was evaluated for its mutagenicity using the Salmonella mutagenicity test (Maron, et al. *Mutation Res.* 113:173–215, 1983).

Sister Chromatid Exchange (SCE) Testing.

SCE was performed to test the ability of AT to induce cytogenetic changes in vitro. The method uses Chinese hamster ovary cells to test chemicals for their ability to induce chromosomal aberrations and sister chromatid exchanges (SCE's ) (Galloway, et al, *Environ. Mol. Mutagenesis.* S10:1–45).

Production of Anti-Reverse Transcriptase Activity.

A bacterial preparation containing anti-reverse transcripatase activity (anti-RT) was obtained as follows. A well-isolated single colony of Pseudomonas species isolate #15 (ATCC No. 55638) was used to inoculate tryptic soy broth. The bacteria were allowed to grow four days stationary phase at 30° C. with gyrorotatory shaking at approximately 40 rpm. The bacteria were then harvested and stored at −20° C. until tested for the presence of a reverse transcriptase inhibitor. Prior to testing, the cultures were sterilized by autoclaving. For each culture to be tested, a 10 ml aliquot was centrifuged for 10 min at 11×g. The pellets were resuspended in 1.5 ml sterile PBS and centrifuged for 10 min. in a sterile Eppendorf tube. The supernatant was examined for the presence of anti-reverse transcriptase activity.

Genprobe Assay for Inhibition of Reverse Transcriptase.

The presence of an inhibitor of reverse transcriptase was assayed using the Gen-Probe assay (Gibco/BRL, Grand Island, N.Y.). The Gen-Probe assay employs a reverse transcription reaction to effect first strand synthesis, followed by amplification of the product by polymerase chain reaction (PCR). Reaction products are detected by agarose gel electrophoresis and staining with ethidium bromide. The presence of a band of approximately 600 base pairs indicates reverse transcriptase activity, whereas the absence of the band indicates inhibition of reverse transcriptase activity.

To test the bacterial preparations for the presence of a reverse transcriptase inhibitor, 5 μl aliquots of each preparation, made as described in the preceding section, were used in a 25-μl reverse transcription reaction volume. The preparation was undiluted or diluted 1:10 or 1:100 using distilled water as the diluent. Following the reverse transcription reaction, a 2 Al aliquot of the reaction mixture was used for the PCR reaction, which was conducted by standard methods in a 20 μl reaction volume. The samples were loaded onto a TBE-1% agarose gel, electrophoretically separated, and stained with EtBr, according to standard methods. Included as a molecular size standard was HaeIII-digested φX174.

The bacterial preparations tested for inhibition of reverse transcriptase included fresh or aged cultures of *Pseudomonas sp.* isolate #15, which were either irradiated or unirradiated. Also included was a preparation from a culture of *Pseudomonas chlororaphis* isolate (ATCC 9446).

RESULTS

Toxicity of AT for LT-1 Cells

The effect of various AT preparations on LT-1 cell viability is summarized in Table 4. Among cells treated with irradiated bacterial whole culture, only 3.4% survived. Cells treated with the pellet exhibited a slight decrease in survival. Approximately 40% of cells treated with the supernatant survived, suggesting that there is some loss of AT activity upon centrifugation at 1040×g. Filtration of AT through a 0.2 μm filter resulted in a slight decrease in the activity of AT. Autoclaving AT at 18 psi for 10 min. decreased toxicity by greater than 50% (data not shown).

TABLE 4

Treatments of AT and Percent Survival of LT-1 Cell Cultures[a]

| Sample (Treatment) | Percent Survival |
|---|---|
| Batch 7 (unirradiated control) | 100.0 |
| Batch 7 (1.5 MR) | 3.4 |
| Batch 7 (1.5 MR, flushed with nitrogen) | 1.9 |
| Batch 7 (1.5 MR, supernate) | 59.6 |
| Batch 7 (1.5 MR, pellet) | 91.7 |

TABLE 4-continued

Treatments of AT and Percent Survival of LT-1 Cell Cultures[a]

| Sample (Treatment) | Percent Survival |
|---|---|
| *Pseudomonas chlororaphis* (1.5 MR) | 0.3 |
| #15 plaque former (1.5 MR) | 5.1 |
| Lyophilized (1.5 MR, rehydrated after irradiation) | 3.7 |
| Lyophilized (1.5 MR, rehydrated before irradiation) | 10.5 |

[a]Addition of 20 μl AT per 1.5 ml medium to each well. The fraction of surviving cells was determined at 1 week after seeding LT-1 cells.

The cytotoxic effect of AT appears to be irreversible, since removal of AT from the cells did not reverse the cytotoxic effect. Additional experiments revealed that lyophilization or flushing with nitrogen, which can be used to nullify production of oxygen radicals by gamma radiation, had little effect on the activity of AT (Table 4). *Pseudomonas chlororaphis* and an isolate designated #15 plaque former also produced a compound which had a detrimental effect on LT-1 cells.

Specificity of AT Toxicity.

AT exhibited marked cell type specificity. As can be seen in Table 5, both human- and rat-derived carcinomas were more sensitive ($LC_{50}$=1.3–3.3 ml $l^{-1}$) than normal rat epithelial cells ($LC_{50}$=26–>53 ml $l^{-1}$). No toxicity was observed when AT was delivered to either human sarcomas or rat fibroblasts ($LC_{50}$>53 ml $l^{-1}$). Normal epithelial cells plated at clonogenic densities, i.e. dispersed, were sensitive to AT when applied at a concentration of 26.6 ml $l^{-1}$. Normal epithelial cells whose growth was confluent were not sensitive to AT (Table 5). This sparing effect in high density cultures were not observed for neoplastic cells (see IC-12, BP-A, Table 5).

Partial characterization of AT.

Results of enzymatic digestion experiments were inconclusive; however, it appeared that amylase and lipoprotein lipase affected the activity of AT, which suggests that AT may have a lipopolysaccharide component. Attempts to isolate AT by lipid extraction and a broad spectrum protocol were unsuccessful, possibly due to destructive drying procedures or harsh chemicals employed. Other extraction procedures are being tested, specifically a phenol extraction method for lipopolysaccharides.

TABLE 5

Lethal Concentration -- 50% of AT for Different Cell Populations[a]

| Cells | $LC_{50}$(ml $1^{-1}$) Dispersed | $LC_{50}$(ml $1^{-1}$) Center Plated |
|---|---|---|
| Rat-Neoplastic | | |
| IC-12 | 1.3 | 1.3 |
| BP-A | 2.3 | 2.3 |
| Rat Preneoplastic | | |
| XR600 | 3.6 | ND[b] |
| IC-1 | | |
| Human Carcinomas | | |
| Hu292 | 2.2 | ND |
| A549 | 3.3 | ND |
| Human Sarcoma | | |
| SA0S2 | >53 | ND |

TABLE 5-continued

Lethal Concentration -- 50% of AT
for Different Cell Populations[a]

| Cells | $LC_{50}$(ml $1^{-1}$) Dispersed | $LC_{50}$(ml $1^{-1}$) Center Plated |
|---|---|---|
| Rat Normal Cells | | |
| Fibroblasts | >53 | >53 |
| Epithelial | 26.6 | >53 |

[a]Cells were plated at clonogenic densities (dispersed) or confluent densities (center plated). AT (0-80 µl per well, 0-53 ml $1^{-1}$) was added to the culture medium 24–48 h. after seeding cultures. At 1 week, cultures were fixed, stained, and surviving cells scored. By extrapolation, the concentration of AT which corresponded to a toxic dose for 50% of the cells was determined.
[b]ND = No Data.

Induction of Apoptosis and Peroxidase by AT.

Peroxidase staining experiments showed that for LT-1 cells and rat fibroblasts, significant liberation of oxygen was observed when $H_2O_2$ was added to cultures previously exposed to AT. Controls cultures not exposed to AT showed no liberation of $O_2$. Osteosarcoma cells, cultures which are insensitive to AT (Table 5), produced oxygen after exposure to $H_2O_2$ whether or not AT was present in the medium. Differential staining showed no evidence of apoptosis in any of the AT exposed cells.

Release of AT from ALZET Pumps and Silastic Pellets in Culture.

In initial experiments utilizing ALZET pumps, ~1.2 µl of AT was released during the first hour. After an additional 30 h., only 0.1 µl AT was released. For this reason, samples were subjected to centrifugation prior to adding the pump to avoid apparent problems with clogging of the pump. The experiment was repeated using the supernatant, and the dose released during the first hour increased to 2.3 µl with 0.4 µl $h_{-1}$ released during the next 30 h.

In the first 6 h. of incubation in experiments with silastic pellets, 8.2 µl (out of a total of 10 µl) leached from the pellet. A total of 9.2 µl leached out by 24 h. Thus, an excessively high dose of AT is delivered early. This leaves little AT in the pellet for long-term release studies in vivo.

Mutagenicity Testing of AT.

Mutagenicity testing of AT demonstrated that cells treated with AT, either with or without S9, were negative for mutagenic effects by the SCE method. Furthermore, AT is nongenotoxic and noncytotoxic as determined by the Salmonella mutagenicity test.

Effects of AT In Vivo.

Rat tracheas containing AT impregnated silastic pellets were implanted subdermally in syngeneic rats. Two weeks after implantation, the tracheas were harvested and evaluated histologically. No evidence of toxic effects on normal epithelium in vivo was noted. Control and AT-exposed tissue were indistinguishable.

Efforts to block tumor cell growth in vivo with AT containing silastic pellets were not successful. This may have been due to the AT release characteristics of silastic pellets and/or due to poor diffusion of AT to all tumor cell populations. Preliminary experiments are currently being carried out to determine whether AT injected directly into the growing tumor in vivo can inhibit growth.

Inhibition of Reverse Transcriptase

Bacterial preparations made from an aged cultures of ATCC No. 55638 were found to inhibit reverse transcriptase. The inhibitory effect appears to be independent of whether the preparation was irradiated, because preparations of both irradiated and unirradiated aged cultures inhibit reverse transcriptase.

We claim:

1. A gamma-irradiated bacterial preparation having anti-tumor activity, wherein the preparation is made from a gamma-irradiated, biologically pure culture of a bacterial isolate having all of the identifying characteristics of Pseudomonas species isolate #15 (ATCC #55638).

2. The bacterial preparation of claim 1, wherein the bacterial isolate is Pseudomonas species isolate #15 (ATCC #55638).

3. A method for producing a bacterial preparation having anti-tumor activity, comprising the steps of:

(a) providing a biologically pure culture of a bacterial isolate having all of the identifying characteristics of Pseudomonas species isolate #15 (ATCC #55638); and (b) exposing the culture of step (a) to a dose of gamma radiation effective to activate the anti-tumor activity.

4. The method of claim 3, wherein the bacterial isolate is Pseudomonas species isolate #15 (ATCC #55638).

5. A method for inhibiting the growth of carcinoma cells comprising delivering an effective amount of the bacterial preparation of claim 1 to the cells.

6. The method of claim 5, wherein the bacterial isolate is Pseudomonas species isolate #15 (ATCC #55638).

7. The preparation of claim 1, wherein the preparation exhibits greater cytotoxicity toward a tumor cell than toward a normal cell.

* * * * *